United States Patent [19]

Grayzel

[11] Patent Number: 4,550,502

[45] Date of Patent: Nov. 5, 1985

[54] DEVICE FOR ANALYSIS OF RECORDED ELECTROCARDIOGRAM

[76] Inventor: Joseph Grayzel, 262 Fountain Rd., Englewood, N.J. 07631

[21] Appl. No.: 485,287

[22] Filed: Apr. 15, 1983

[51] Int. Cl.$^4$ ............................ A61B 5/04; G01B 3/02
[52] U.S. Cl. ...................................... 33/1 B; 33/1 C; 128/702; 128/706
[58] Field of Search ................................ 128/702–706, 128/710; 33/1 B–1 C, 174 D

[56] References Cited

U.S. PATENT DOCUMENTS

| | | | |
|---|---|---|---|
| 846,006 | 3/1907 | Bryson | 33/1 B |
| 1,232,290 | 7/1917 | Grunsberg | 33/1 B |
| 1,876,431 | 9/1932 | Page | 33/1 C |
| 2,088,533 | 7/1937 | Phelps | 128/710 X |
| 2,501,550 | 3/1950 | Tamagna et al. | 33/1 C |
| 3,812,586 | 5/1974 | Itokawa | 33/1 C |
| 4,023,276 | 5/1977 | Furukawa et al. | 33/1 C |
| 4,030,486 | 6/1977 | Eastman | 33/1 C |
| 4,282,655 | 8/1981 | Tinman | 33/1 C |
| 4,388,759 | 6/1983 | Orejola | 33/1 C |

Primary Examiner—Lee S. Cohen
Assistant Examiner—Angela D. Sykes
Attorney, Agent, or Firm—Edward R. Weingram

[57] ABSTRACT

A gauge which facilitates the analysis of a recorded electrocardiogram which comprises a flat sheet of transparent material having a plurality or fan of straight diverging lines disposed on said sheet; a plurality of straight, parallel lines disposed on the sheet extending in a direction transverse to the diverging lines and perpendicular to a line extending medially between the outermost of said diverging lines, said diverging lines intersecting said parallel lines as to define equal increments along any parallel line; the transverse lines being spatially arranged such that they intersect with the diverging lines to form a grid therewith wherein the distance between adjacent points of intersection with the diverging lines on any of the parallel lines bear a relation to the heart beat rates or heart rate cycle interval of a periodic wave form recorded on an electrographic chart or strip; indicia means disposed on said sheet for designating the transverse parallel lines as graduations of a scale comprising intervals which correspond to said heart rate cycle intervals or heart beat rates; and the gauge being physically sized so that said diverging lines are laterally spaced apart to encompass at least two heart beat cycles of said periodic wave form.

8 Claims, 15 Drawing Figures

DEVICE FOR ANALYSIS OF RECORDED ELECTROCARDIOGRAM

FIELD OF THE INVENTION

The present invention relates to the analysis of a recorded electrocardiogram (ECG) and more particularly, to a device which facilitates analysis of the recorded electrocardiogram to aid in the diagnosis of the cardiac rhythm, and other features of the ECG record, and the method of using the same.

BACKGROUND OF THE INVENTION

An electrocardiograph is an instrument to be applied to the human body for the purpose of making a gram or recorded line for indicating the operations of the heart, such as the expansion and contraction of the heart muscle, which is accompanied by electric currents. The electrocardiograph records the changes of electrical potential occurring in the form of a tracing on a paper chart or strip divided into blocks 1.0 mm square, which are representative of units of time.

The normal heart rate of an adult is considered to lie between 60 and 100 beats/minute. Slower rates often enable the emergence of extra, irregular beats and a transition to a very rapid heart rate and fast heart rates, often described as palpitations of the heart, may follow irregular beating and produce weakness, fatigue, anxiety and faintness. The ultimate danger from all types of alterations in the rhythm of the heartbeat or cardiac arrhythmias is their possible progression to cardiac arrest and sudden death.

The great variety and number of cardiac rhythmic disturbances and diseased rhythmic mechanisms point up the magnitude of the diagnostic problem facing the physician who must make a definitive diagnosis before selecting a medication to treat the arrhythmia. Also, with the variety of anti-arrhythmic medications available, each possessing its own mode of action and nuance of effect, precise diagnosis of the arrhythmia is most important for selection of optimum therapy.

In view of the magnitude of the problem of accurate diagnosis and matching the medication to the arrhythmia, the need for a diagnostic tool or aid for the study of arrhythmias recorded on the conventional electrocardiographic (ECG) chart or strip would appear to be evident.

Heretofore, various scales for determining the average heart rate based on 2-beat or 3-beat counts have been available, but these have no applicability to the diagnosis of arrhythmias. A device generally used is a caliper or divider, an instrument which can be adjusted to the interval of a single heart beat. However, it is limited in use to examining one beat at a time and then comparing one beat to the next. Thus, the caliper does not provide for simultaneous analysis of a group or sequence of beats so that the rhythm created by the sequence of beats could be observed and any departure from regularity would be immediately revealed.

Moreover, various time intervals on the ECG waveform are of importance, such as heart rate, cycle duration, the time from onset of the P-wave to onset of the QRS wave (PR interval), and the time from onset of the QRS wave to the end of the T-wave (QT interval). For the physician to evaluate these intervals for abnormalities requires several measurements and corrections made by calculations or use of reference tables, none of which steps are quick or convenient.

Thus, the development of a device or diagnostic tool which would enable analysis of a group or sequence of beats simultaneously so as to provide ready means for determining the regularity of the rhythm of the heart beats would not only be highly desirable but of significant importance. Furthermore, the desirability of such a device that could also combine means for conveniently diagnosing other characteristics of the ECG waveform, must be obvious.

BRIEF DESCRIPTION OF THE DISCLOSURE

In accordance with the present invention, there is provided a gauge which facilitates the analysis of a group or sequence of heart beats recorded on an electrocardiogram to diagnose the cardiac rhythm which comprises a flat sheet of transparent material having:

(a) a plurality or fan of straight diverging lines disposed on said sheet (b) a plurality of straight parallel lines disposed on said sheet extending in a direction transverse to said diverging lines and perpendicular to a line extending medially between the outermost of said diverging lines, said diverging lines being angularly spaced with respect to one another as to intercept equal increments along each particular horizontal line, said transverse lines being spatially arranged such that they intersect with said diverging lines to form a grid therewith wherein the distance between adjacent points of intersection with said diverging lines on any of the parallel lines bears a relation to the heart beat rate or heart cycle interval of a periodic waveform recorded on an electrocardiographic chart;

(c) indicia means disposed on said sheet for designating the transverse parallel lines as graduations of a scale comprising intervals which correspond to said heart beat cycle interval or heart beat rate; and (d) said gauge being physically sized so that the outermost of said diverging lines are laterally spaced apart to encompass at least two heart beat cycles of said periodic waveform.

DESCRIPTION OF THE PREFERRED EMBODIMENT

Figure 1:
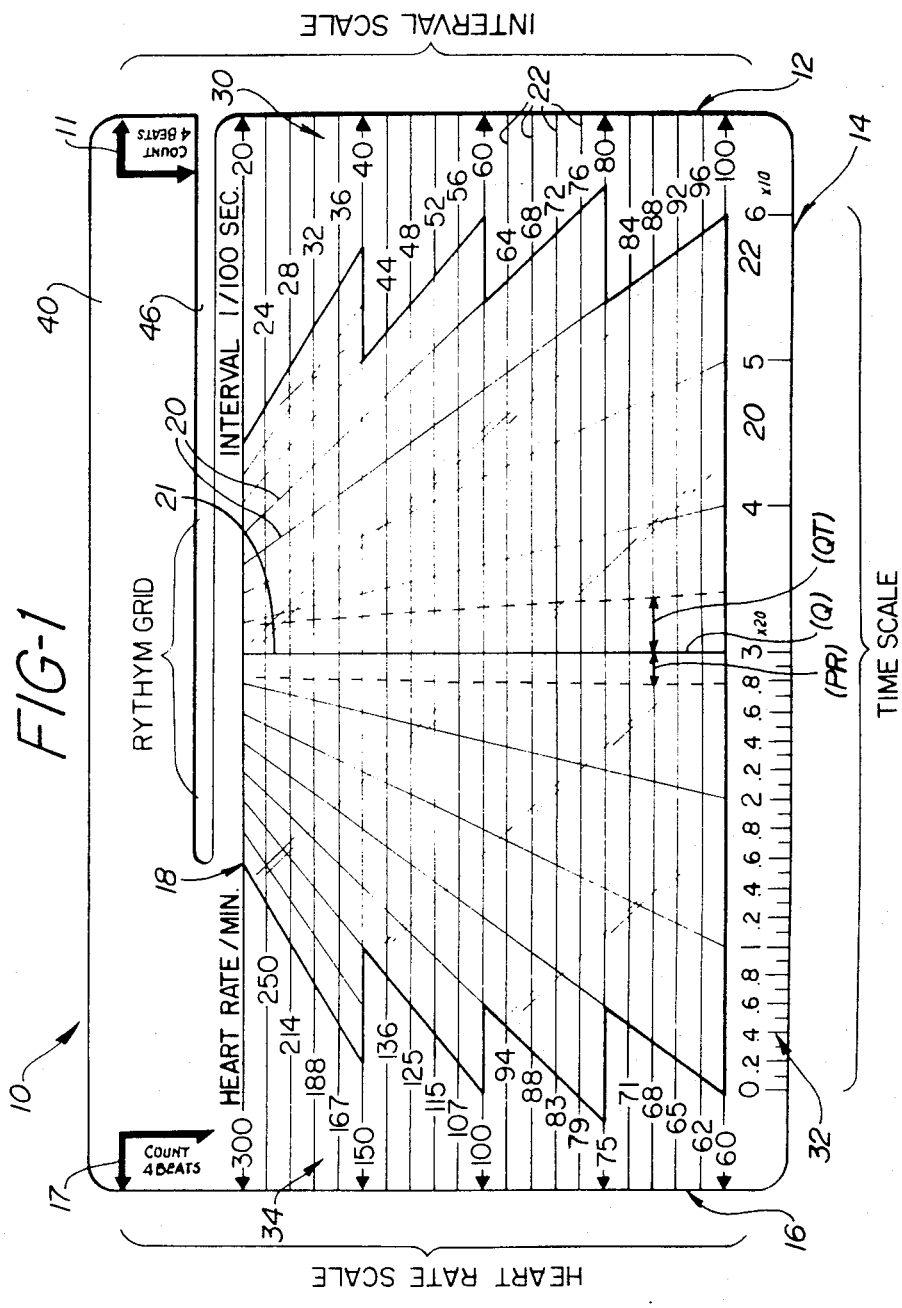
FIG. 1 is a plan view of a flat transparent sheet gauge having a geometrically arranged set of lines and indicia located according to the invention for analysis of the rhythm of a sequence of heart beats recorded on an electrocardiogram.

Turning now to the drawings wherein like reference numerals denote like parts, there is shown in FIG. 1 an exemplary embodiment of the transparent sheet gauge (Rhythm Rule) of the present invention designated generally as 10 having a plurality of lines geometrically placed so that by using the gauge, analysis of the cardiac rhythm and other features of an electrocardiograph (ECG) record of a series of heart beats can be made simultaneously. The gauge comprises a rectangular sheet of transparent flat material formed of a suitable clear plastic or the like.

The gauge 10 has a first indexed straight edge 12 identified as the "Interval Scale", a second indexed straight edge 14 identified as the "Time Scale", and a third indexed straight edge 16 identified as the "Heart Rate Scale". Imprinted on the face thereof is a scale or rhythm grid 18 which is defined by a plurality or fan of diverging straight lines 20, which if projected in the direction of convergence would be found to radiate from a common point upon or remote from the sheet. The rhythm grid 18 further comprises a plurality of straight parallel lines 22, preferably, equally spaced apart, extending between the first straight edge 12 and the third straight edge 16 in a direction transverse to the radiating lines 20 and perpendicular to a line 21 medially between the outermost of said radiating lines. The diverging lines 20 are angularly spaced with respect to one another as to intercept equal increments along each particular horizontal line 22. In the illustrated embodiment, as one specific example, such medial line conforms to the central radiating line 21, and the transverse lines are laterally spaced apart from each other so as to encompass therebetween substantially the full length of the radiating lines. Further in this example, the radiating lines 20 are spaced apart at their closest ends a distance of 0.5 centimeter and at their furthest apart ends a distance of 2.5 centimeters, and the transverse lines 22 are equally spaced apart a distance of 4.0 mm.

The gauge 10 further comprises indicia means disposed on the sheet for designating the transverse parallel lines 22 as graduations of a scale 30 disposed along the first indexed straight edge 12 comprising one or more 1/100 sec intervals and as graduations of a scale 34 disposed along the third indexed straight edge 16 comprising one or more heart beats/min. Indicia means are also disposed on the sheet for designating the second indexed straight edge as graduations of a scale 32 comprising one or more seconds in 0.1 second intervals. More particularly, the illustrated gauge is adapted for use with an electrocardiographic recording paper speed at 25 mm/sec and is based on a 4-heart beat count. Accordingly, the indicia means for the first indexed straight edge 12 designates the parallel lines as graduations of a scale 30 extending in a direction from a zero-point arrow 11 comprising one or more 1/100 of a second intervals with each graduation having 4/100 of a second spacing; the indicia means for the third indexed straight edge 16 designates the parallel lines as graduations of a scale 34 that extends from a zero-point arrow 17 comprising heart beat rates/min between 300 to 60; and the indicia means for the second indexed straight edge 14 designates the graduations of a time scale 32 comprising 6 seconds, three seconds of which have 0.1 second graduations. Also, the physical size of the gauge as described above is designed so that the particular rate at which the radiating or diverging lines 20 of the rhythm grid 18 diverge provides for the creation of cooperating graduations of the first, second and third indexed straight edges. The particular rate at which the radiating lines 20 diverge is based upon the length of a periodic waveform depicting four heart beats recorded on an electrocardiographic chart or strip.

Cooperation between the angular increments of divergence of lines 20 of the rhythm grid 18 and the spacing between adjacent intersecting points on parallel line 22 with the scales for heart rate 34 and/or cycle interval 30 is created from the relationship of the ECG recording papers speed of 25 mm/sec and the length of the recorded waveform wherein 25 mm=1.0 second. Thus, a recorded heartbeat of 60 beats/min which is equivalent to 1 beat/sec, can be represented by a spacing of 25 mm between adjacent intersecting points on the parallel transverse line. The recorded heart rate of 60 beats/min indexed on scale 34 corresponds to a heart beat cycle interval of 1.0 second indexed on scale 30 with such indexed points on the opposing scales 30 and 34 being connected by a parallel transverse line having a spacing between adjacent intersecting points of 25 mm. Similarly, a heart beat rate of 75 beats/min indexed on scale 34 corresponds to an interval of 0.8 seconds indexed on scale 30 and is connected with a transverse line having a spacing between adjacent intersecting points of 20 mm; a heart rate of 100 (scale 34) corresponds to an interval of 0.6 seconds (scale 30) and the interconnecting parallel line has a spacing of 15 mm between adjacent intersecting points.

Gauges of the invention could be readily provided with similar cooperating features between the Interval 30 and Heart Rate 34 scales and a Rhythm Grid 18 based on other beat-counts by changes in overall size of such gauge. Alternatively, it will be understood that the horizontal and/or vertical divergence of the rhythm grid 18 can be varied so that fewer or, preferably, longer recorded ECG waveforms will be encompassed by the diverging lines of grid scale 18 without providing for direct cooperation with other measurement scales. Adding additional diverging lines 20 would encompass a greater number of beats and increasing the angular increments of divergence may provide for advantages in other diagnostic situations.

Figure 10A:
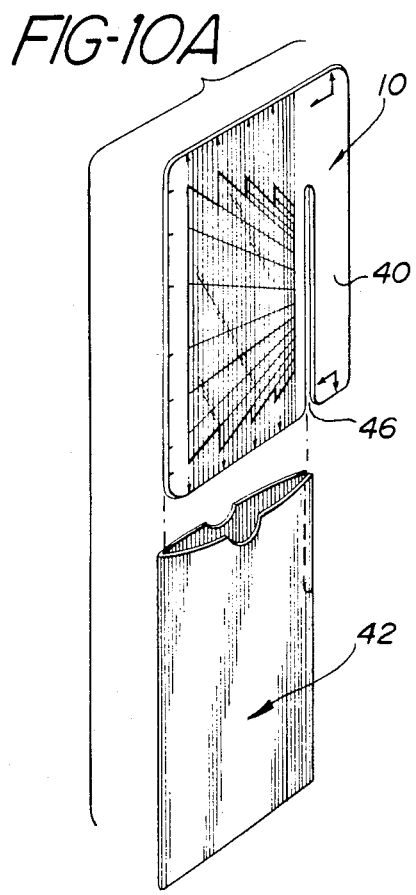
FIG. 10A is a perspective view of the gauge of FIG. 1 and a slipcase for said gauge.
Figure 10B:
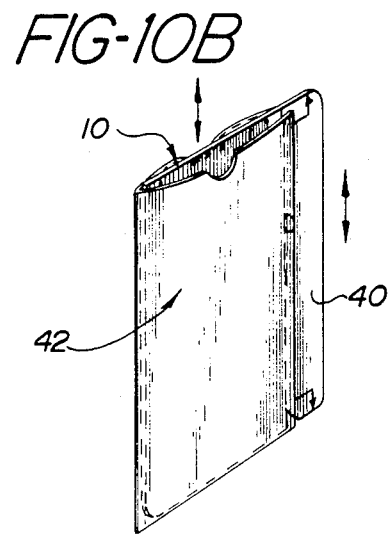
FIG. 10B is a perspective view of the gauge of FIG. 1 inserted into the slipcase of FIG. 10A.
Figure 11:
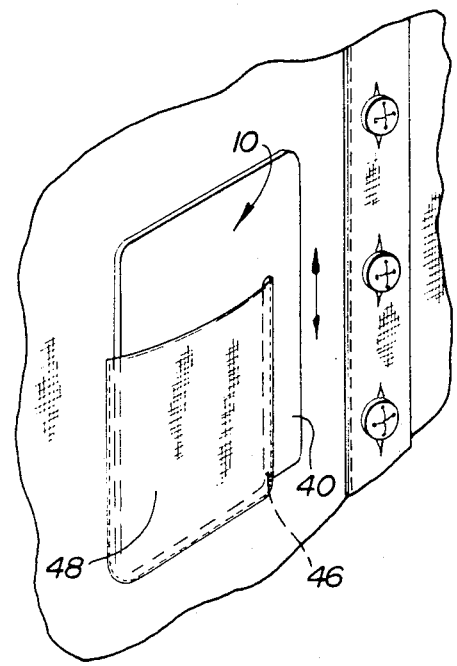
FIG. 11 is a fragmentary perspective view of an article of clothing showing a breast pocket with the slip case of FIG. 10A containing the gauge of FIG. 1 inserted therein.

The illustrated gauge 10 is also, preferably, of a physical size so that it may be carried by a physician in a shirt pocket or the breast pocket of a smock. In this connection, there is illustrated in FIGS. 10A and 10B a protective slip case 42 that can be fabricated from plastic, paper and the like, into which the gauge 10 may be inserted. To facilitate carrying of the encased gauge and prevent it from being inadvertently ejected from the protective slip case or pocket, said gauge 10 is provided with a tongue portion 40 which is not inserted into the slip case. From the gauge 10 adjacent and generally parallel with the fourth straight edge of the gauge 10 is cut out a narrow, elongated section of material which forms an elongated slit 46. When the gauge 10 is inserted into the protective slip case 42 as illustrated in FIG. 10B, the tongue portion 40 of said gauge is not encased. Then, when the encased gauge is inserted into a pocket 48, as illustrated in FIG. 11, the opposing sides of the slit 46 engage the fabric sides of the pocket providing a friction clip which restrains any inadvertent ejection of the gauge from either the pocket or the slip case.

As will become apparent from the following description, it is desirable to include a sufficient number of radiating or diverging lines on the gauge to permit the simultaneous analysis of as large a group of recorded heart beats in a waveform as possible and thus readily diagnose the rhythm of such heart beats. The number of diverging lines is chosen to encompass the series of heart beats that can be simultaneously analyzed and in the illustrated embodiment, fifteen diverging lines are employed to nominally encompass at least a 4 to 6 beat count, but depending on the heart rate and length of the record, could encompass up to 15 beats simultaneously for analysis as a group.

The operation or use of the rhythm rule or gauge 10 of the invention will be described as a series of steps using the various scales that are available to assist in the analysis of an ECG waveform. As will be obvious, many of the steps can be accomplished in any order or may be used independently from other steps to evaluate specific problems or make independent analysis.

Figure 2:
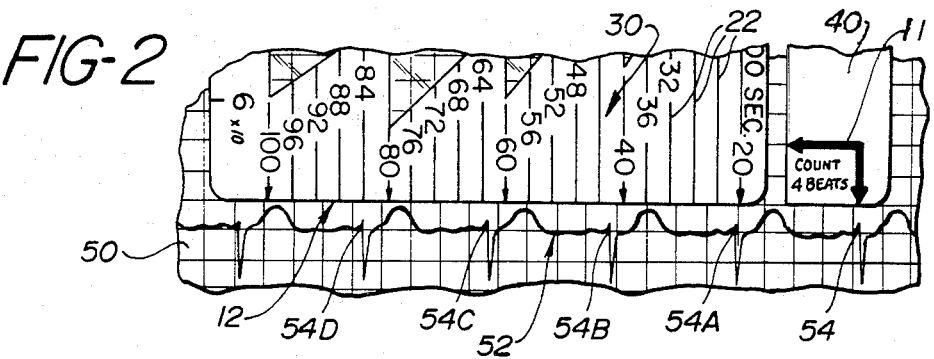
FIG. 2 is a fragmentary plan view of the gauge of FIG. 1 in use to measure the cycle length of a sequence of heart beats recorded on an electrocardiogram.
Figure 3:
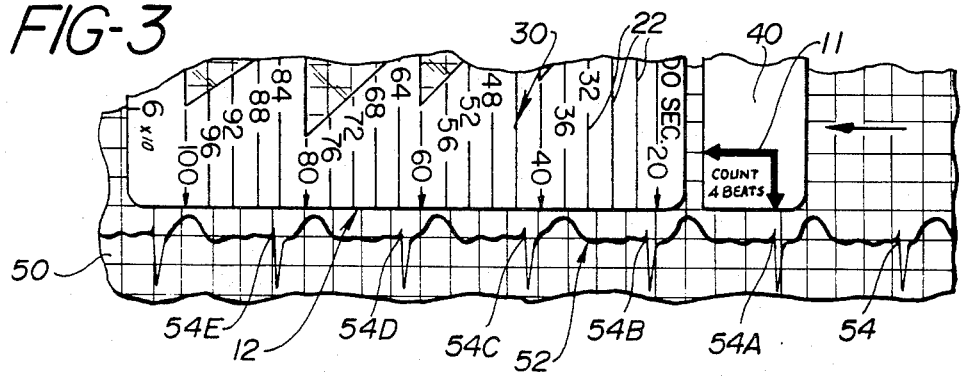
FIG. 3 is a fragmentary plan view of the gauge of FIG. 1 in use to measure the cycle length of a sequence of heart beats recorded on the electrocardiogram of FIG. 2.

The FIGS. 2 and 3 illustrate the method for accurately determining the average cycle duration for a sequence of beats in an ECG waveform recorded on an ECG chart, the corresponding Heart Rate in beats/min, the cycle length of each beat and variations in cycle length. In FIG. 2 the first indexed straight edge 12 of the gauge 10 is placed over the ECG chart 50 with the zero-point arrow 11 of scale 30 aligned with the onset of a QRS complex 54 on an ECG tracing 52. Four cycles of the tracing (waveform) 52 are counted (to QRS complex 54D); the reading from scale 30 is the average cycle duration in hundreds of a second or in seconds. Moving from this value across the gauge 10 to the Heart Rate scale 34 on the third indexed straight edge 16 gives the corresponding Heart Rate in beats per minute.

The interval scale 30 can also be used to determine variations in cycle length. After the average cycle length for a sequence of four beats (from QRS 54 to 54D) is determined as shown in FIG. 2, the zero point arrow 11 is moved ahead one beat (FIG. 3) to the onset of QRS complex 54A on the tracing 52. Four cycles are counted to the onset of the fourth QRS complex 54E in the sequence of beats, thus measuring the average cycle length of these 4-beats. If the reading of the average cycle length has changed, the difference represents ¼ of the difference in cycle length between beats 1 and 5.

Figure 4:
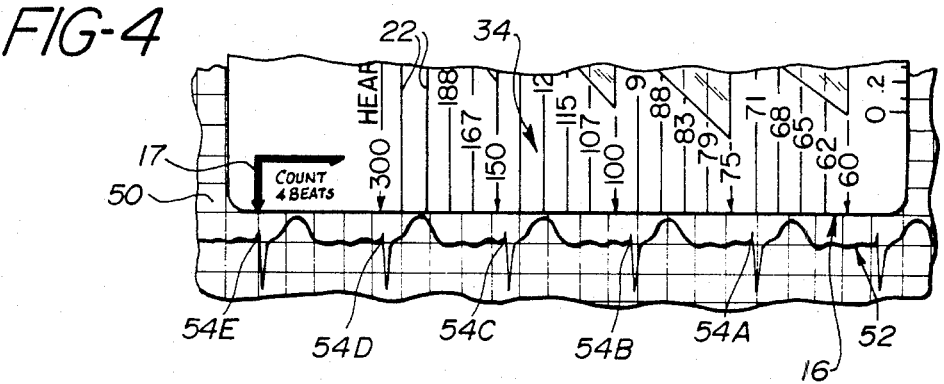
FIG. 4 is a fragmentary plan view of the gauge of FIG. 1 in use to measure the heart beat rate of a sequence of heart beats recorded on the electrocardiogram of FIG. 2.

FIG. 4 illustrates the method for accurately determining the heart rate in beats per minute for a sequence of beats. In FIG. 4, the third indexed straight edge 16 of the gauge 10 is placed over the ECG chart 50 with the zero point arrow 17 of scale 34 indexed on some prominent point of the QRS complex 54E. Four cycles in the ECG tracing are counted, to QRS complex 54A, and the heart rate of 71 beats per minute can be read directly from the scale 34.

Figure 5:
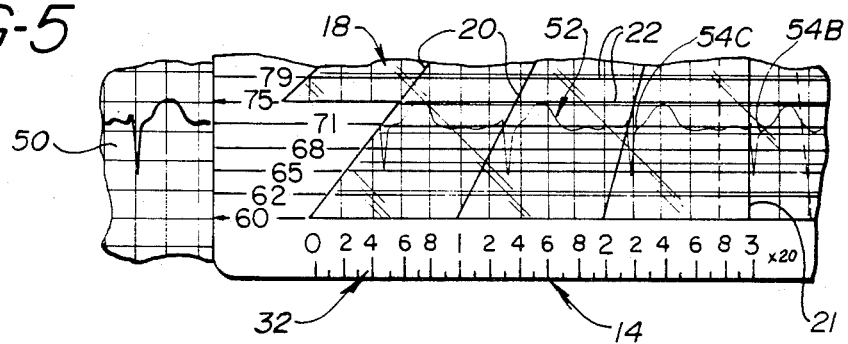
FIG. 5 is a fragmentary plan view of the gauge of FIG. 1 in use to measure the regularity of rhythm of a sequence of heart beats recorded on the electrocardiogram of FIG. 2.

FIG. 5 illustrates the method for simultaneously analyzing the regularity of the rhythm of a sequence of 4-heart beat cycles recorded on an ECG tracing. In FIG. 5, the gauge 10 is placed over the ECG chart 50 with the parallel line 22 corresponding to the heart rate of 71 beats/min (determined as described above and illustrated in FIG. 4) placed along the baseline of the ECG tracing 52. The central diverging line 21 is aligned with the onset of a QRS complex 54B from the middle of the group of beats being analyzed. The onset of other QRS complexes is compared with the regular intersection of diverging lines 20 and the parallel lines 22 corresponding to a heart rate of 71 beats/min. In the illustrations shown in FIG. 5, the QRS complexes fall exactly on the intersections indicating that the heart rate was regular at 71 beats/min.

Figure 6A:
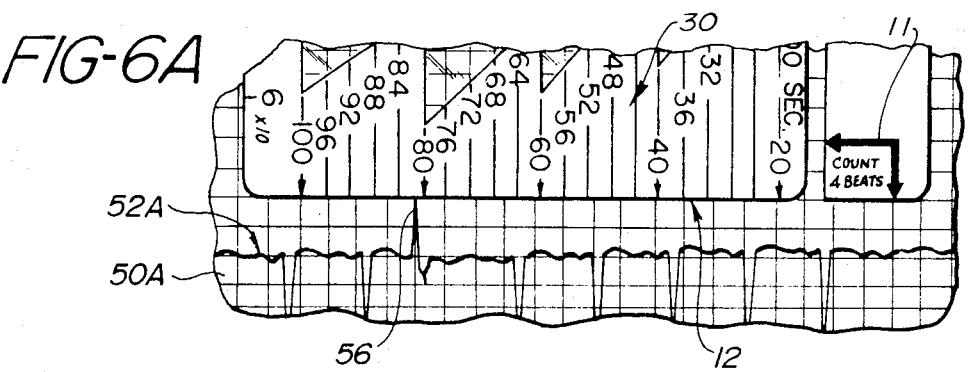
FIG. 6A is a fragmentary plan view of the gauge of FIG. 1 in use to measure the cycle length of a sequence of heart beats recorded on an electrocardiogram.
Figure 6B:
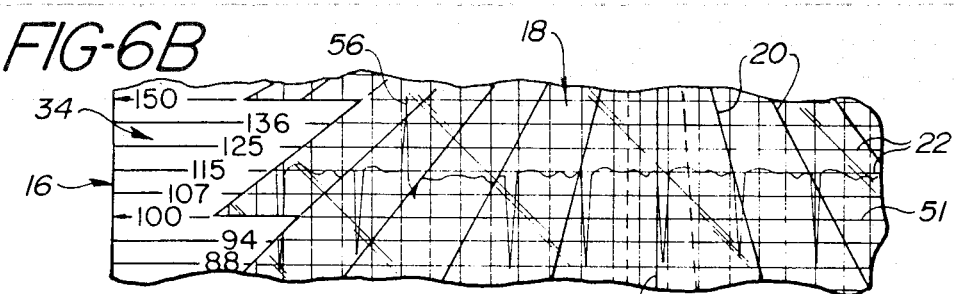
FIG. 6B is an enlarged fragmentary plan view of the gauge of FIG. 1 in use to measure the regularity of rhythm of a sequence of heart beats recorded on the electrocardiogram of FIG. 6A.
Figure 6C:
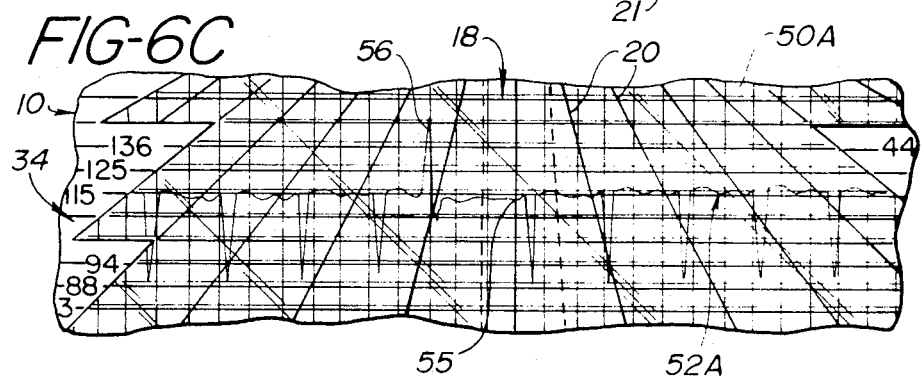
FIG. 6C is a fragmentary plan view of the gauge of FIG. 1 in use to measure the regularity of rhythm of a different wave segment of the sequence of heart beats recorded on the electrocardiogram of FIG. 6A.

In FIGS. 6A, 6B, and 6C is illustrated another important use for the gauge of the invention, analysis of the regularity of a sequence of beats containing a ventricular premature beat (VPB) and the search for buried P-waves obscured by the VPB. In FIG. 6A, the interval scale 30 along the first indexed straight edge 12 of gauge 10 is used to determine the average cycle duration of a sequence of 4 beats. Using the method described above and illustrated in FIGS. 2 and 3, the average cycle interval was determined to be 52/100 (scale 30) for an ECG tracing 52A on the ECG chart 50A. The parallel line 22 corresponding to the interval 52/100 (115 beats/min) is placed along the baseline of the ECG wave form 52A with the central diverging line 21 aligned with a typical QRS complex. The other QRS complexes of supraventricular type in the sequence of beats being analyzed align with the diverging lines 20, indicating that the sinus mechanism is very regular. One VPB 56, is seen in the sequence of beats and analysis of the sequence of beats shows that the sinus mechanism of the wave form is not disturbed by the VPB.

In FIG. 6C, the gauge is used to search for buried P-waves on the tracing 52A obscured by the VPB 56. Using the transverse parallel line 52/100, the gauge is moved so that the central diverging line 21 and other diverging lines coincide with the onset of the P-waves 55. The regularity of the P-wave at a heart rate of 115 beats/min is shown. Also shown is the occurrence of the obscured P-wave which falls within the VPB complex.

Figure 7A:
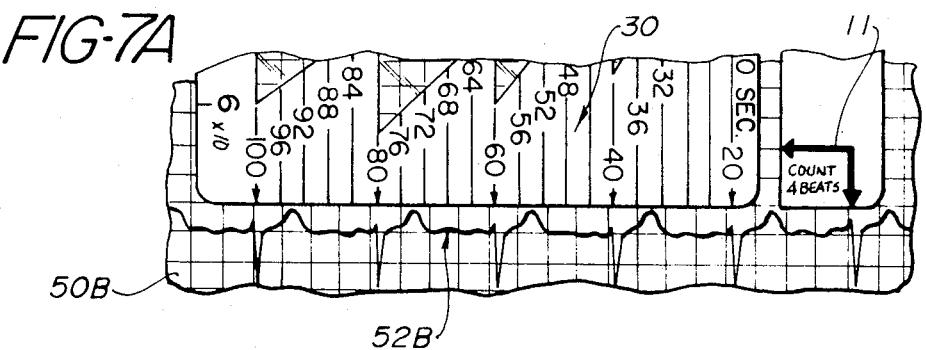
FIG. 7A is a fragmentary plan view of the gauge of FIG. 1 in use to measure the cycle length of a sequence of heart beats recorded on an electrocardiogram strip.
Figure 7B:
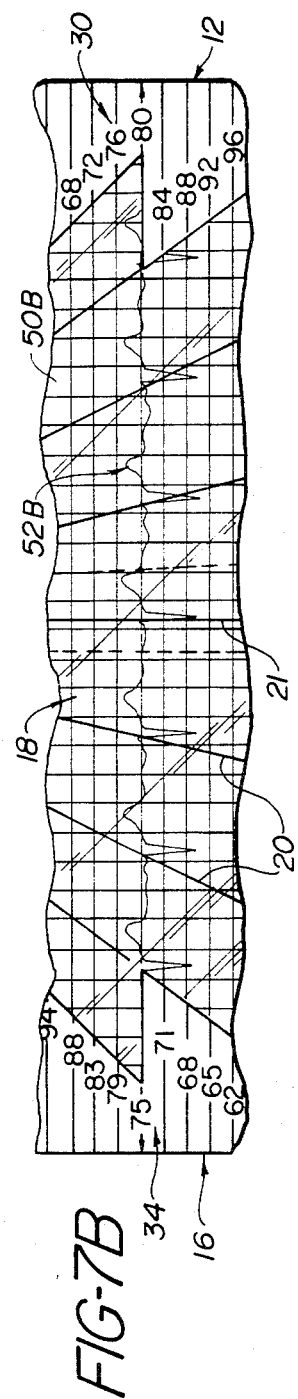
FIG. 7B is an enlarged fragmentary plan view of the gauge of FIG. 1 in use to measure the regularity of rhythm of a sequence of heart beats recorded on the electrocardiogram strip of FIG. 7A.

In FIGS. 7A and 7B is illustrated the use of the gauge for a heart rate and interval whose values are not precisely shown on the graduations of the Heart Rate 34 and Interval 30 scales. In FIG. 7A, the zero point arrow 11 of the Interval scale 30 is placed on a QRS complex in the ECG tracing 52B and 4 cycles are counted. The fiducial point of the fourth QRS complex in tracing 52B falls just past the value of 80 on the Interval scale 30, indicating an average cycle duration of 81/100 (the corresponding Heart Rate is about 74 beats/min, also not shown on the Heart Rate scale 34). While a parallel line 22 (rate-interval line) does not exist for this value, precise resolution of the rhythm can be made as illustrated in FIG. 7B by placing the ECG tracing 52B baseline parallel to the rate-interval line for an interval of 80 from the Interval scale 30, but slightly below; to be precise, 1.0 mm below, as shown in FIG. 7B. In FIG. 7B it is illustrated that the diverging lines 20, radiating about central line 21 of the Rhythm Grid 18, align with the onset of QRS complexes in a sequence of beats on ECG trace 52B.

Figure 8:
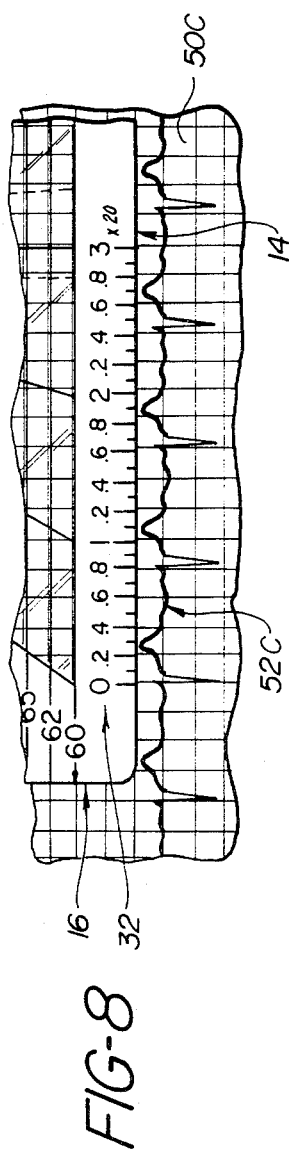
FIG. 8 is a fragmentary plan view of the gauge of FIG. 1 in use to measure the duration of a single cycle of a typical beat recorded on electrocardiogram strip.

The second indexed straight edge 14 of the gauge 10 provides a time scale 32 for the ECG recorded at 25 mm/sec. Six seconds are represented on the time scale 32. To measure a single-cycle length the zero-point of the time scale 32 is indexed with a QRS complex of a typical beat in the ECG trace 52C and the duration of a single cycle is measured. This value is then located on the Interval scale 30 of the gauge and the corresponding heart rate is read on the Heart Rate scale 34. As shown in FIG. 8, the time scale 32 applied to a typical beat in trace 52C measures a cycle length of 0.81 or 81/100 second. The closest value on the Interval scale 30 is 80/100 with a corresponding heart rate of 75 beats/min. Thus, by simple interpolation, a measured interval of 81/100 has a corresponding heart rate of 74 beats/min.

Figure 9:
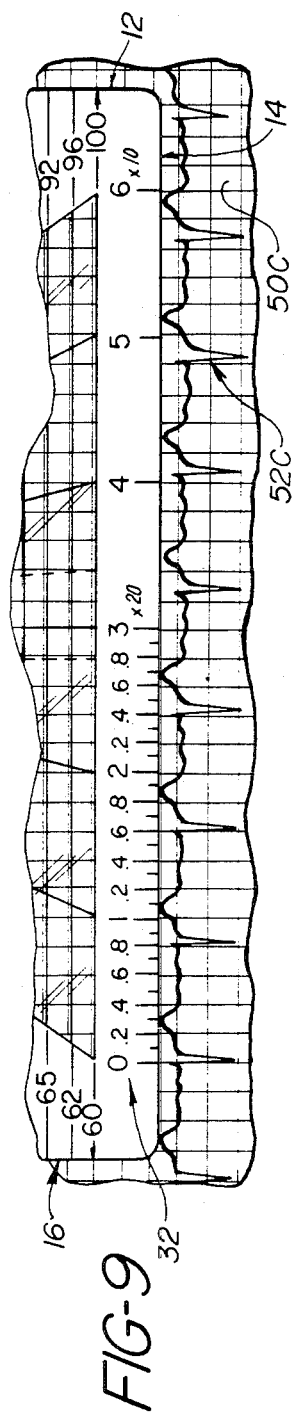
FIG. 9 is an enlarged fragmentary plan view of the gauge of FIG. 1 in use to measure the number of beat cycles within a time frame in a sequence of heart beats recorded on the electrocardiogram strip of FIG. 8.

The time scale 32 can be used to quickly determine the beat rate of a sequence of beats in an ECG tracing. In FIG. 9 is illustrated the method for carrying out such determination. As shown in FIG. 9, the time scale 32 is placed along an ECG trace 52C with the zero-point directly on a QRS. Counting cycles to the 6-second mark on the true scale determines 7 full plus a fraction of 0.4 which equals 7.4 cycles. This reading is then multiplied by ten to give a heart rate of 74 beats/min.

As has been previously mentioned, a further time interval of importance on the ECG waveform is the time from onset of the P-wave to onset of QRS wave, i.e. the PR interval. This is important as an indicator of heart block, a condition that may lead to cardiac arrest. Another interval, the time from onset of the QRS wave to the end of the T-wave, the QT interval, is important since its prolongation indicates a susceptibility to lethal arrhythmias. Both the PR and QT intervals, particularly the latter, normally vary with the heart rate. In the past, for the physician to evaluate these intervals, he had to first measure the interval, then determine the heart rate, and finally correct the measured value for the heart rate to ascertain normality or abnormality. The correction had to be done either by mathematical formula or by reference to a table, neither of which is quick or convenient. In the present invention, however, the grid incorporates numerical scales which read the heart rate and cycle duration, and at each level of heart rate possesses visual markers for the normal PR and QT interval, such that upon placing the template for the Rhythm Grid over the ECG record, the heart rate, cycle duration, PR interval and QT interval are immediately evaluated simultaneous with diagnosis of the arrhythmic mechanism of the heart.

Thus, in FIG. 1, the transparency of the grid permits the proper Rate-Interval line to be super-imposed on the baseline of the ECG. If the baseline is tilted, the Rate-Interval line can be tilted. The central vertical ray (Q) is aligned with the onset of a typical QRS complex chosen from the middle of the group being analyzed. The onset of each complex can be compared with the regularity of the ray intersections along the Rate-Interval line, and even the smallest variations can be noted.

At the same time, the PR and QT intervals can be quickly assessed at the center of the Rate-Interval line. With the central vertical ray placed at the onset of a QRS complex, the dashed line to the left of the vertical indicates the upper limits of normal for PR, and the dashed line to the right of the vertical indicates the upper limit of normal for the QT interval.

While in the foregoing specification embodiments of the invention have been set forth in considerable detail for purposes of making a complete disclosure thereof, it will be apparent to those skilled in the art that numerous changes may be made without departing from the spirit and principle of the invention.

What is claimed is:

1. A gauge which facilitates the analysis of a recorded electrocardiogram which comprises a flat sheet of transparent material having:
    (a) a plurality of straight diverging lines disposed on said sheet with the lines being spaced apart at equal angular increments;
    (b) a plurality of straight, parallel lines disposed on said sheet extending in a direction transverse to said diverging lines and perpendicular to a line extending medially between the outermost of said diverging lines, said diverging lines intersecting said parallel lines as to define equal increments, along a given parallel line, and said transverse lines being spatially arranged such that they intersect with said diverging lines to form a grid therewith wherein the distance between adjacent points of intersection with said diverging lines on any of the parallel lines bear a relation to the heart beat rates or heart rate cycle interval of a periodic wave form recorded on an electrographic chart or strip;
    (c) indicia means disposed on said sheet for designating the transverse parallel lines as graduations of a scale comprising intervals which correspond to said heart rate cycle intervals or heart beat rates; and
    (d) said gauge being physically sized so that said diverging lines are laterally spaced apart to encompass at least two heart beat cycles of said periodic wave form.

2. The gauge of claim 1 wherein said indicia means comprise a scale means coacting with said straight parallel lines to determine the heart beat rate of a sequence of beats on a periodic wave form recorded on an electrographic chart or strip.

3. The gauge of claim 1 wherein said indicia means comprise scale means coacting with said straight parallel lines to determine the heart rate cycle interval of a sequence of beats on a periodic wave form recorded on an electrographic chart or strip.

4. The gauge of claim 1 wherein the distance along each parallel line between the points of intersection of said diverging lines is equal so that said points of intersection of said grid can be used to determine the degree of regularity of the cardiac rhythm and the pattern of any irregularity over a sequence of at least two heart beat cycles.

5. A gauge in accordance with claim 1, wherein said sheet is generally rectangular and includes a longitudinally extending slit toward one long edge thereof, thereby providing a flexible tongue between said slit and edge for frictionally engaging the clothing of a user when the remainder of the gauge is inserted into said user's pocket.

6. A gauge and slipcase combination comprising:
 (a) a gauge which facilitates the analysis of a recorded electrocardiogram which comprises a flat sheet of transparent material having:
  (i) a plurality of straight diverging lines disposed on said sheet with the lines being spaced apart at equal angular increments;
  (ii) a plurality of straight, parallel lines disposed on said sheet extending in a direction transverse to said diverging lines and perpendicular to a line extending medially between the outermost of said diverging lines, said diverging lines intersecting said parallel lines as to define equal increments, along a given parallel line, and said transverse lines being spatially arranged such that they intersect with said diverging lines to form a grid therewith wherein the distance between adjacent points of intersection with said diverging lines on any of the parallel lines bear a relation to the heart beat rates or heart rate cycle interval of a periodic wave form recorded on an electrographic chart or strip;
  (iii) indicia means disposed on said sheet for designating the transverse parallel lines as graduations of a scale comprising intervals which correspond to said heart rate cycle intervals or heart beat rates;
  (iv) said gauge being physically sized so that said diverging lines are laterally spaced apart to encompass at least two heart beat cycles of said periodic wave form;
  (v) wherein said sheet is generally rectangular and includes a longitudinally extending slit toward one long edge thereof, thereby providing a flexible tongue between said slit and edge for frictionally engaging the clothing of a user when the remainder of the gauge is inserted into said user's pocket; and
 (b) a slip case having a slit extending on one side thereof, said slip case receiving said gauge with said tongue extending from said case slit whereby said encased gauge can be inserted into a user's pocket and retained frictionally by said protruding tongue.

7. A method for accurately determining the degree of regularity of the cardiac rhythm over a sequence of beats in a periodic waveform recorded on an ECG tracing, said method comprising:
 the steps of placing a transparent sheet gauge over a periodic waveform recorded on an ECG tracing, with the sheet having a scale disposed thereon which is defined by a plurality of straight diverging lines which are spaced apart so as to provide continuously variable spacing capable of matching a periodic waveform of any cycle length or repetition rate;
 aligning the scale with respect to the periodic waveform such that the diverging lines intersect with respective segments on a sequence of cycles on said periodic waveform, and with the base line of said waveform extending perpendicularly to a line extending medially between the outermost diverging lines; and
 comparing the regularity of the intersections of the diverging lines with the respective segments of a sequence of cycles on said waveform.

8. A method for accurately determining the degree of regularity of the cardiac rhythm over a sequence of beats in a periodic waveform recorded on an ECG tracing, said method comprising the steps of:
 determining the cycle length or heartbeat rate of a periodic waveform recorded on an ECG tracing;
 placing a transparent sheet gauge over said ECG tracing, with the sheet having a scale disposed thereon, which is defined by a plurality of straight diverging lines and a plurality of straight parallel lines which extend in a direction transverse to the diverging lines and perpendicular to a line extending medially between the outermost of said diverging lines, said diverging lines intersecting said parallel lines as to define equal increments on a given parallel line, and indicia for designating the transverse parallel lines as graduations of a scale comprising cycle interval or hearbeat rate;
 aligning one of the straight parallel lines corresponding to the determined cycle length or heart rate of said periodic waveform with respect to the base line of the periodic waveform in such a position that the outermost of the diverging lines intersecting said straight parallel line intersects with respective segments on a sequence of cycles of said periodic waveform; and
 comparing the regularity of intersection of the diverging lines with the straight parallel line with respective segments of a sequence of beats, and thereby accurately determining the regularity of cardiac rhythm of a series of beats in a periodic waveform.

* * * * *